United States Patent
Phanstiel, IV et al.

(10) Patent No.: US 11,752,113 B2
(45) Date of Patent: Sep. 12, 2023

(54) POLYAMINE TRANSPORT INHIBITORS AS ANTIVIRALS

(71) Applicants: UNIVERSITY OF CENTRAL FLORIDA RESEARCH FOUNDATION, INC., Orlando, FL (US); TRUSTEES OF BOSTON UNIVERSITY, Boston, MA (US)

(72) Inventors: Otto Phanstiel, IV, Orlando, FL (US); John Connor, Boston, MA (US)

(73) Assignees: University of Central Florida Research Foundation, Inc., Orlando, FL (US); Boston University, Boston, MA (US)

( * ) Notice: Subject to any disclaimer, the term of this patent is extended or adjusted under 35 U.S.C. 154(b) by 0 days.

(21) Appl. No.: 17/469,827

(22) Filed: Sep. 8, 2021

(65) Prior Publication Data
US 2022/0071928 A1 Mar. 10, 2022

Related U.S. Application Data

(60) Provisional application No. 63/076,058, filed on Sep. 9, 2020.

(51) Int. Cl.
| | | |
|---|---|---|
| A61K 31/132 | (2006.01) |
| A61K 31/198 | (2006.01) |
| A61K 31/13 | (2006.01) |
| A61K 31/155 | (2006.01) |
| A61K 31/404 | (2006.01) |
| A61K 31/16 | (2006.01) |
| A61P 31/12 | (2006.01) |
| A61K 31/4706 | (2006.01) |
| A61K 31/522 | (2006.01) |
| A61K 31/4985 | (2006.01) |
| A61K 31/505 | (2006.01) |
| A61K 31/513 | (2006.01) |
| A61K 31/675 | (2006.01) |

(52) U.S. Cl.
CPC .......... *A61K 31/132* (2013.01); *A61K 31/13* (2013.01); *A61K 31/155* (2013.01); *A61K 31/16* (2013.01); *A61K 31/198* (2013.01); *A61K 31/404* (2013.01); *A61K 31/4706* (2013.01); *A61K 31/4985* (2013.01); *A61K 31/505* (2013.01); *A61K 31/513* (2013.01); *A61K 31/522* (2013.01); *A61K 31/675* (2013.01); *A61P 31/12* (2018.01)

(58) Field of Classification Search
CPC .............................. A61K 31/132; A61K 31/137
See application file for complete search history.

(56) References Cited

U.S. PATENT DOCUMENTS

| | | |
|---|---|---|
| 6,949,679 B1 | 9/2005 | Poulin et al. |
| 8,497,398 B1 | 7/2013 | Phanstiel, IV et al. |
| 9,212,131 B2 * | 12/2015 | Phanstiel ............ C07D 295/13 |
| 9,598,351 B2 | 3/2017 | Phanstiel, IV |
| 9,730,902 B2 * | 8/2017 | Phanstiel, IV ....... A61K 31/166 |
| 2012/0172449 A1 | 7/2012 | Phanstiel et al. |
| 2014/0057989 A1 | 2/2014 | Phanstiel, IV |
| 2016/0311756 A1 | 10/2016 | Phanstiel, IV et al. |

FOREIGN PATENT DOCUMENTS

WO    WO-2018107027 A1 *    6/2018    ........... A61K 31/135

OTHER PUBLICATIONS

Alexander, Eric T. et al., "A novel polyamine blockade therapy activates an anti-tumor immune response", Oncotarget, 2017, vol. 8, No. 48, pp. 84140-84152.
Burns, Mark R. et al., "Amino Acid/Spermine Conjugates: Polyamine Amides as Potent Spermidine Uptake Inhibitors", J. Med. Chem., 2001, pp. 44, pp. 3632-3644.
Burns, Mark R. et al., "Lipophilic Lysine-Spermine Conjugates Are Potent Polyamine Transport Inhibitors for Use in Combination with a Polyamine Biosynthesis Inhibitor", J. Med. Chem., 2009, vol. 52, pp. 1983-1993.
Chen, Yan et al., "Combination therapy with 2-difluoromethylornithine and a polyamine transport inhibitor against murine squamous cell carcinoma", Int. J. Cancer: vol. 118, pp. 2344-2349, 2006.
Dobrovolskaite, Aiste et al., "A discovery of indolone GW5074 during a comprehensive search for non-polyamine-based polyamine transport inhibitors", International Journal of Biochemistry and Cell Biology, vol. 138, 2021, 13 pages.
Gardner, Richard Andrew et al., "N1-Substituent Effects in the Selective Delivery of Polyamine Conjugates into Cells Containing Active Polyamine Transporters", J. Med. Chem., 2004, vol. 47, pp. 6055-6069.
Gitto, Sarah B. et al., "Difluoromethylornithine Combined with a Polyamine Transport Inhibitor Is Effective against Gemcitabine Resistant Pancreatic Cancer", Mol. Pharmaceutics, 2018, vol. 15, pp. 369-376.
Graminski, Gerard F. et al., "Synthesis of Bis-Spermine Dimers that are Potent Polyamine Transport Inhibitors", Bioorganic & Medicinal Chemistry Letters, vol. 12, 2002, pp. 35-40.
Grossi, Mario et al., "Inhibition of Polyamine Uptake Potentiates the Anti-Proliferative Effect of Polyamine Synthesis Inhibition and Preserves the Contractile Phenotype of Vascular Smooth Muscle Cells", J. Cell. Physiol., vol. 231, pp. 1334-1342, 2016.
Hayes, Candace S. et al., "Polyamine-Blocking Therapy Reverses Immunosuppression in the Tumor Microenvironment", Cancer Immunol Res, vol. 2, No. 3, Mar. 2014.
Hayes, Candace S. et al., "Polyamine blockade promotes antitumor immunity", OncoImmunology, vol. 3, Jan. 2014, 3 pages.

(Continued)

Primary Examiner — James D. Anderson
(74) Attorney, Agent, or Firm — Timothy H. Van Dyke; WOLTER, VAN DYKE, DAVIS, PLLC

(57) ABSTRACT

Disclosed herein are polyamine transport inhibitors (PTI) and methods of use as antivirals. Disclosed PTI compounds are useful as treatments for viral infections or can be used as prophylactic agents that protect high risk individuals from becoming infected by the virus. The disclosed PTI compounds can be used alone or in combination with other agents (or other antivirals) to improve patient outcomes such as DFMO (or Remdesivir).

12 Claims, 7 Drawing Sheets

(56) References Cited

OTHER PUBLICATIONS

Kaur, Navneet et al., "Designing the Polyamine Pharmacophore: Influence of N-Substituents on the Transport Behavior of Polyamine Conjugates", J. Med. Chem., 2008, vol. 51, pp. 2551-2560.

Kaur, Navneet et al., "A Comparison of Chloroambucil- and Xylene-Containing Polyamines Leads to Improved Ligands for Accessing the Polyamine Transport System", J Med. Chem., 2008, vol. 51, pp. 1393-1401.

Kurihara, Shin et al., "Putrescine Importer PlaP Contributes to Swarming Motility and Urothelial Cell Invasion in Proteus mirabilis", The Journal of Biological Chemistry vol. 288, No. 22, pp. 15668-15676, May 31, 2012.

Lewis, John R. et al., "Polyamine Inhibitors for Treatment of Feline Oral Squamous Cell Carcinoma: A Proof-of-Concept Study", J Vet Dent, vol. 30, No. 3, Fall 2013, pp. 140-145.

Madan, Meenu et al., "ATP13A3 and caveolin-1 as potential biomarkers for difluoromethylornithine-based therapies in pancreatic cancers", Am J Cancer Res, 2016, vol. 6, No. 6, pp. 1231-1252.

Mastrodomenico, Vincent et al., "Polyamine Depletion Inhibits Bunyavirus Infection via Generation of Noninfectious Interfering Virions", Journal of Virology, Jul. 2019, vol. 93, Issue 14, 19 pages.

Mounce, Bryan C. et al., "Inhibition of Polyamine Biosynthesis Is a Broad-Spectrum Strategy against RNA Viruses", Journal of Virology, Nov. 2016, vol. 90, No. 21, pp. 9683-9692.

Mounce, Bryan C. et al., "Interferon-Induced Spermidine-Spermine Acetyltransferase and Polyamine Depletion Restrict Zika and Chikungunya Viruses", Cell Host & Microbe, vol. 20, pp. 167-177, 2016.

Mounce, Bryan C. et al., "Polyamines and Their Role in Virus Infection", Microbiology and Molecular Biology Reviews, Dec. 2017, vol. 81, Issue 4, 12 pages.

Muth, Aaron et al., "Development of Polyamine Transport Ligands with Improved Metabolic Stability and Selectivity against Specific Human Cancers", J. Med Chem. 2013, vol. 56, pp. 5819-5828.

Muth, Aaron et al., "Polyamine Transport Inhibitors: Design, Synthesis, and Combination Therapies with Difluoromethylornithine", J. Med. Chem. 2014, vol. 57, pp. 348-363.

Niemand, Jandeli et al., "Anthracene-Polyamine Conjugates Inhibit In Vitro Proliferation of Intraerythrocytic Plasmodium falciparum Parasites", Antimicrobial Agents and Chemotherapy, Jun. 2013, vol. 57, No. 6 pp. 2874-2877.

Olsen, Michelle E. et al., "Differential Mechanisms for the Involvement of Polyamines and Hypusinated eIF5A in Ebola Virus Gene Expression", Journal of Virology, Oct. 2018, vol. 92, Issue 20, 15 pages.

Park, Myung Hee et al., "Hypusine, a polyamine-derived amino acid critical for eukaryotic translation", J. Biol. Chem., 2018, vol. 293, No. 48, pp. 18710-18718.

Pegg, Anthony E. et al., "Functions of Polyamines in Mammals", Journal of Biological Chemistry, vol. 291, No. 29, Jul. 15, 2016, 14904-14912.

Phanstiel IV, O. et al., "Structure-activity investigations of polyamine-anthracene conjugates and their uptake via the polyamine transporter", Amino Acids, 2007, vol. 33, pp. 305-313.

Phanstiel IV, Otto et al., "Design of Polyamine Transport Inhibitors as Therapeutics", RSC Drug Discovery Series, No. 17, 2012, pp. 162-190.

Raina A. et al., "Role of Polyamines in the Replucation of Animal Viruses", Medical Biology, vol. 59, 1981, pp. 428-432.

Samal, Katherine et al., "AMXT-1501, a novel polyamine transport inhibitor, synergizes with DFMO in inhibiting neuroblastoma cell proliferation by targeting both ornithine decarboxylase and polyamine transport", Int. J. Cancer, 2013, vol. 133, pp. 1323-1334.

Skorupski, K.A. et al., "Phase I/II clinical trial of 2-difluoromethylornithine (DFMO) and a novel polyamine transport inhibitor (MQT 1426) for feline oral squamous cell carcinoma", Veterinary and Comparative Oncology, 2011, vol. 9, No. 4, pp. 275-282.

Sutherland, C. Simone et al., "A Literature Review of Economic Evaluations for a Neglected Tropical Disease: Human African Trypanosomiasis ("Sleeping Sickness")", PLOS Neglected Tropical Diseases, Feb. 5, 2015, 22 pages.

Tate, Patrick M. et al., Ribavirin Induces Polyamine Depletion via Nucleotide Depletion to Limit Virus Replication, Cell Reports, vol. 28, pp. 2620-2633, Sep. 3, 2019.

Traquete, Rui et al., "Ant 4,4, a polyamine-anthracene conjugate, induces cell death and recovery in human promyelogenous leukemia cells (HL 60)", Amino Acids, 2013, vol. 44, pp. 1193-1203.

Tsen, Chung et al., "A *Drosophila* Model to Identify Polyamine-Drug Conjugates That Target the Polyamine Transporter in an Intact Epithelium", J. Med. Chem., 2008, vol. 51, pp. 324-330.

Tyms, A.S. et al., "Inhibitors of polyamine biosynthesis block human cytomegalovirus replication", Nature, vol. 297, Jun. 24, 1982, pp. 690-691.

\* cited by examiner

Native polyamines
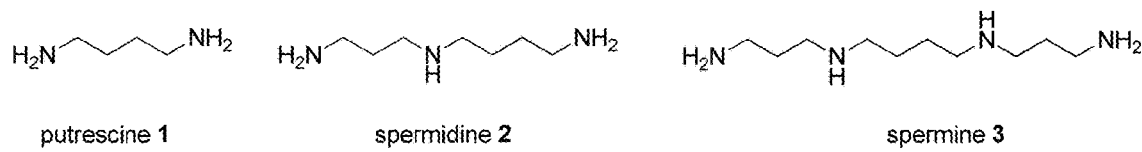
putrescine 1        spermidine 2        spermine 3
Other drugs
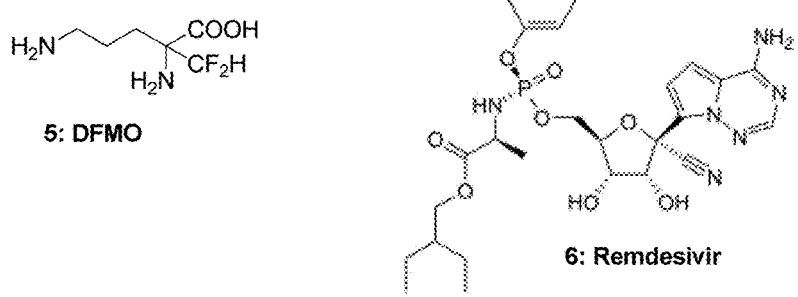
5: DFMO
6: Remdesivir
FIG. 1

15: R=H; 6 HCl (Triamide44, x=y=4)
16: R=(CH$_2$)$_4$NH$_2$; 9 HCl (Triamide444, x=y=4)
17: R=(CH$_2$)$_3$NH$_2$; 9 HCl (Triamide343, x=3, y=4)

Polyamine Sequence (R):

R = -NH(CH$_2$)$_4$NH(CH$_2$)$_4$NHMe
(4,4 sequence)

$$\left[ \text{alternative sequences} \atop R=\text{-NH(CH}_2)_4\text{NH(CH}_2)_3\text{NHMe, } R=\text{-NH(CH}_2)_5\text{NH(CH}_2)_4\text{NHMe} \right]$$
(4,3)           (5,4)

Di-substituted controls

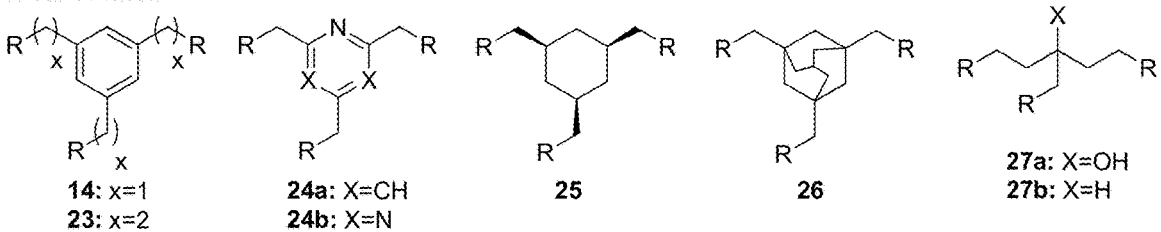

18a: x=1    19    20a: cis    21a: x=1    22
18b: x=2          20b: trans   21b: x=2

Tri-substituted

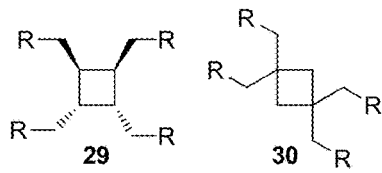

14: x=1    24a: X=CH    25    26    27a: X=OH
23: x=2    24b: X=N                       27b: X=H

Tetra-substituted                   Penta-substituted

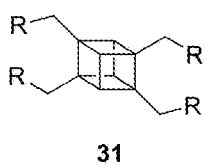
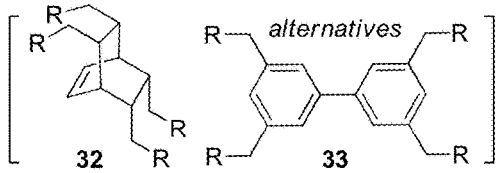

28    29    30           34

31    32    33 (alternatives)

Or a pharmacologically acceptable counterion(s) such as chloride or other halides, or carboxylates like caprate or other linear carboxylic acid salts. Different polyamine arms can be used to modify potency (see polyamine (R) definitions above).

FIG. 3

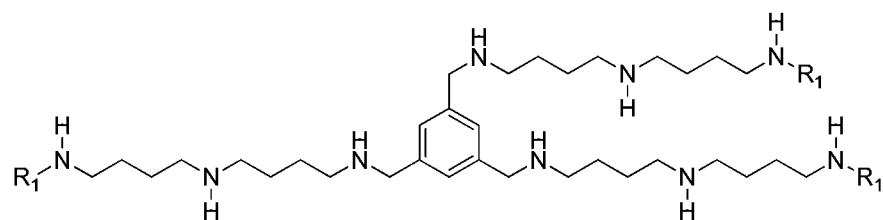

14: trimer44NMe PTI; $R_1$= Me, 9 HCl
Note: 14b is trimer44 PTI; $R_1$=H, 9 HCl

Di-substituted

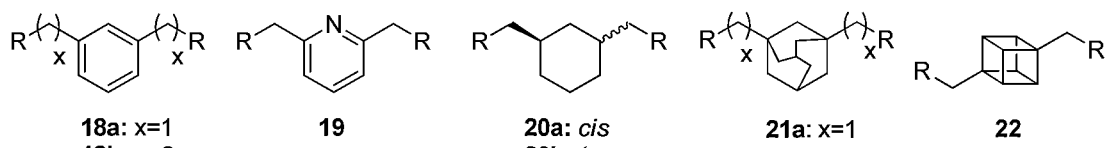

18a: x=1
18b: x=2
19
20a: *cis*
20b: *trans*
21a: x=1
21b: x=2
22

Tri-substituted

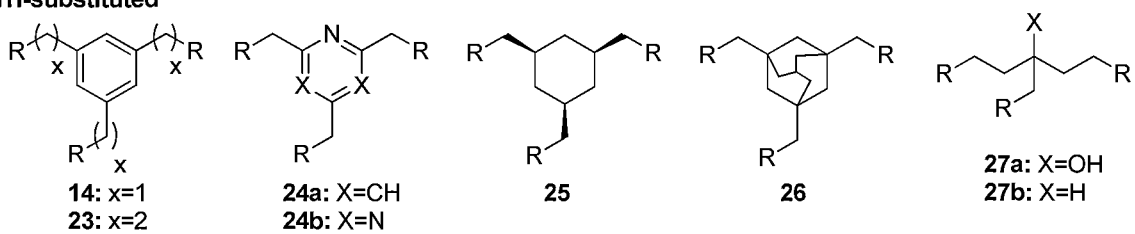

14: x=1
23: x=2
24a: X=CH
24b: X=N
25
26
27a: X=OH
27b: X=H

Tetra-substituted      Penta-substituted

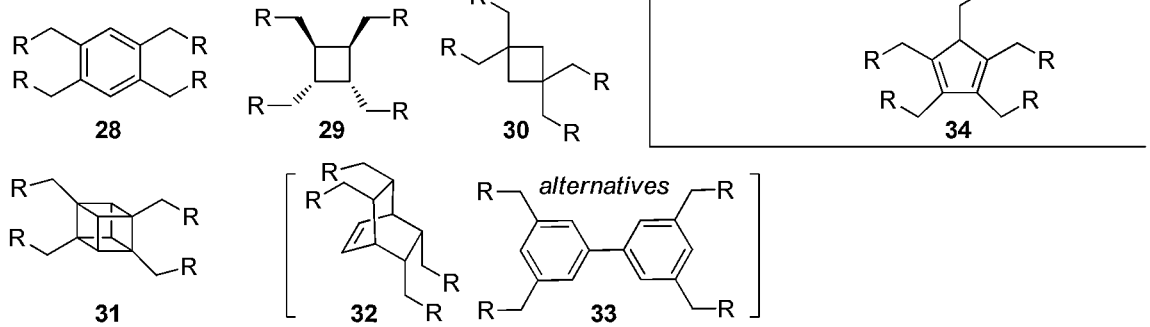

28   29   30   34

31   32   33

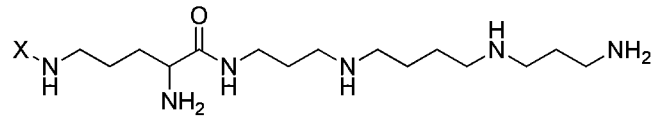

35: X= H, Lys-Spm
36: AMXT-1501, where X= palmitoyl (linear $C_{15}H_{31}$-C=O)

where the polyamine sequence R is one of the following:

Polyamine Sequence (R):

R = -NH(CH$_2$)$_4$NH(CH$_2$)$_4$NHMe
(4,4 sequence)

*alternative sequences*
R=-NH(CH$_2$)$_4$NH(CH$_2$)$_3$NHMe,   R=-NH(CH$_2$)$_5$NH(CH$_2$)$_4$NHMe
(4,3)                    (5,4)

and a pharmacologically acceptable anion is present like Cl$^-$, or a carboxylate group like caprate

FIG. 6

POLYAMINE TRANSPORT INHIBITORS AS ANTIVIRALS

GOVERNMENT SUPPORT

This invention was made with Government support under agency contract/grant nos. W81XH-12-1-0433 awarded by the Department of Defense and AI135517 awarded by the National Institutes of Health. The Government has certain rights in this invention.

BACKGROUND

Current approaches to treating COVID19 (the disease caused by SARS-CoV2 virus) include host targeting molecules such as the antimalarial hydroxychloroquine and innate immune response dampeners such as IL-6 inhibitors and IL-1 inhibitors all the way to small molecule nucleoside analogs like Remdesivir. Indeed, the world has tried many different therapies most to no avail.

BRIEF DESCRIPTION OF THE DRAWINGS

FIG. 1. Structures of the native polyamines 1-3, the polyamine biosynthesis inhibitor DFMO, and antiviral agent Remdesivir FIG. 2. Structures of other polyamine based PTIs.

FIG. 3. Structures of new PTI designs predicated upon the lead PTI 14. These platforms explore how spacing, 3D positioning, angular orientation, and the number of polyamine arms impact the performance of the polyamine transport inhibitor as antivirals. All of these can be made from the commercially available carboxylic acids, converted to the respective aldehydes (or via the mesylate from the respective alcohol) and coupled to the Boc-protected amines as shown in Scheme 1. Final Boc-group removal can be performed using 4M HCl in EtOH.

FIG. 6. Structures of other PTIs

DETAILED DESCRIPTION

Overview

Figure 2:
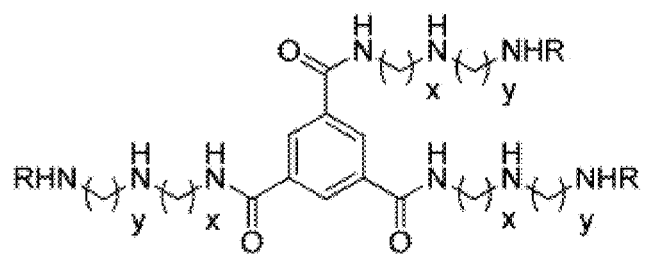

Polyamines play diverse roles in cells including key roles in translation, transcription, chromatin remodeling, autophagy, growth, eIF5A formation, and the immune response. One approach to inhibit viral growth is to starve cells of their polyamine resources. Since many viruses are dependent upon the host to translate viral proteins, polyamine depletion impacts the host cells' ability to translate viral proteins. Polyamine pools are maintained by a balance of polyamine biosynthesis and transport. Polyamine depletion can be accomplished by the combination of a polyamine biosynthesis inhibitor and a polyamine transport inhibitor. A combination therapy is often needed in treating human cancers because proliferating cells when treated with a polyamine biosynthesis inhibitor alone often circumvent the biosynthesis inhibitor by increasing import of exogenous polyamines to maintain intracellular polyamine pools. Virtually all known polyamine transport inhibitors are based upon polyamine scaffolds and work via competitive inhibition of polyamine import. In short, these work by out-competing the native polyamines (putrescine, spermidine and spermine) for cell entry. In this regard, polyamine transport inhibitors compete and inhibit all modes of polyamine import. We have discovered that viruses such as SARS-Cov2 are susceptible to inhibitors of polyamine transport. This patent describes the invention of using polyamine transport inhibitors (PTI) as anti-viral agents. Accordingly, it is demonstrated that targeting polyamine metabolism is a proven antiviral strategy.

Certain organisms are wholly dependent on polyamine import for their survival and are, thus, very sensitive to blockade of polyamine import. We have also shown that PTI compounds (that are polyamine based) can inhibit the growth of parasitic protozoa like *T. cruzi* (Chantal Reigada, Otto Phanstiel I V, Mariana R. Miranda, and Claudio A. Pereira. Targeting polyamine transport in *Trypanosoma cruzi*. *Eur. J. Med. Chem.* 2018, 147, 1-6). Since *T. cruzi* is responsible for Chagas disease, these new PTI agents could provide new medicines for treating Chagas disease and other parasitic protozoan infections by blocking the ability of the parasite to import polyamines. Other organisms like *P. falciparum* (the malarial parasite) have the ability to both make and import polyamines. In another application, the combination of DFMO+PTI can starve microorganisms of the polyamines needed for their growth and could provide novel anti-infective agents. The PTIs can also affect swarming behavior of *Proteus mirabilis* (Putrescine importer PlaP contributes to swarming motility and urolithelial cell invasion in *Proteus mirabilis*. Kurihara, S.; Sakai, Y.; Suzuki, H.; Muth, A.; Phanstiel, O.; Rather, P. N. *J. Biol. Chem.* 2013, 288, 15668-15676). Since *P. mirabilis* is present in urinary tract infections in humans, these new compounds may have utility as antibiotics. The DFMO+PTI also affects vascular remodeling (Inhibition of Polyamine Uptake Potentiates the Anti-Proliferative Effect of Polyamine Synthesis Inhibition and Preserves the Contractile Phenotype of Vascular Smooth Muscle Cells. Grossi, M.; Phanstiel, O.; Rippe, K.; Sward, K.; Alajbegovic, A.; Albinsson, S.; Forte, A.; Persson, L.; Hellstrand, P.; Nilsson, B-O. *J. Cell. Physiol.* 2015, 9999, 1-9). As such the DFMO+PTI therapy could provide a viable approach for targeting unwanted vascular cell proliferation in vivo, including vascular restenosis.

Figure 5:
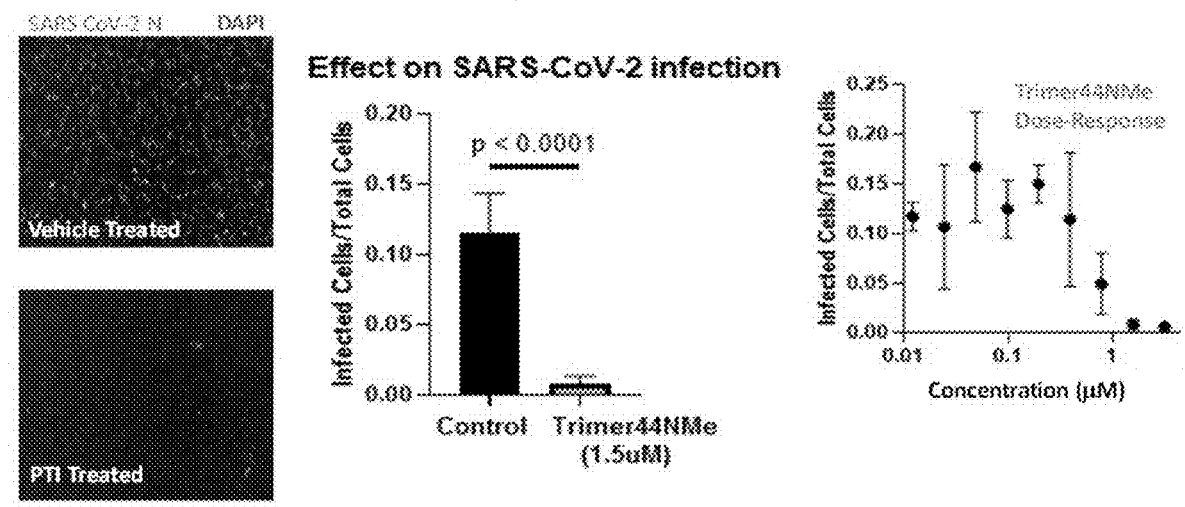
FIG. 5. Inhibition of SARS-CoV2 infection by the trimer44NMe PTI 14. Vero cells were incubated with the Trimer44NMe PTI for 1 h prior to infection with SARS-CoV-2 (WA1 isolate) at a MOI of ~0.5. 24 h post-infection. Cells were then fixed, permeabilized, and stained for viral replication using an antibody for the SARS-CoV-2 viral nucleoprotein to identify infected cells. A near complete blockade of SARS-CoV-2 replication was observed (left panel, and represented in the middle bar graph). Error bars represent SEM of three replicates. PTI 14 IC50 value was ~700 nM from the dose response curve in the right side panel.

Polyamines play important roles in transcription, translation, cell cycle, and immune responses.[1-2] The cationic polyamines are known to interact with RNA, and they have been repeatedly implicated in viral replication.[3-4] Viruses require polyamines from their host cell for multiple stages in the viral life cycle, including DNA-dependent RNA polymerization, genome replication, and viral protein translation.[5-6] Polyamine homeostasis can be targeted by inhibiting polyamine biosynthesis with difluoromethylornithine (DFMO) and polyamine import with a polyamine transport inhibitor (PTI).[7] DFMO has been shown to reduce viral titers across several types of RNA viruses in culture[8] including MERS-CoV replication and demonstrates that blockade of polyamine synthesis by DFMO disrupts coronavirus replication.[6,9] Addition of exogenous polyamines allowed viral replication to recover, however,[8] suggesting that polyamine import can be an activated pathway to replace host cell polyamine pools. FIG. 5 suggests that inhibitors of polyamine transport can act as antivirals that block viral replication. In addition, combination therapies involving DFMO and PTI are also expected to serve as antiviral therapy and are known to invoke an immune response, which in itself could provide antiviral activity in vivo.[10-12]

According to certain embodiments, disclosed are methods and compositions provide a prophylactic therapy to protect people at high risk from catching the virus and even might be able to treat patients with the virus.

Based on the discoveries outlined herein, PTI compounds could be used as treatments for viral infections or could be used as prophylactic agents that protect high risk individuals from becoming infected by the virus. These compounds could be used alone or in combination with other agents (or other antivirals) to improve patient outcomes such as DFMO (or Remdesivir). Depending upon the optimum delivery/route of administration, the approach of delivery can take one of several forms. In one example, PTIs could be formulated into a lozenge that subjects at risk place in their mouth. This can be used by medical caregivers or others when they enter a high-risk area. Also, the PT's could be formulated for parenteral administration such as an intramuscular daily shot where high-risk individuals receive a once a day formulation that protects them from the virus. Another example pertains to an inhalable formulation such as an inhalable mist to be inhaled via an inhaler device into the deep lung for subjects at risk for SARS-CoV2 infections.

Description of Exemplary Embodiments

The invention develops polyamine transport inhibitors as novel antiviral agents. The approach involves targeting the intracellular pools of the native polyamines putrescine 1, spermidine 2 and spermine 3 (FIG. 1). Currently, the polyamine biosynthesis inhibitor (difluoromethylornithine, DFMO 5) has been shown to deplete polyamine pools in human cells and these cells often respond by upregulating polyamine import to replenish their intracellular polyamine pools.[13] One way to block this escape pathway is via a polyamine transport inhibitor (PTI). The combination of DFMO+PTI has shown to be very effective in depleting cells of their polyamine pools and modulating the immune response in various cancer models in vivo.[10-13]

Figure 4:
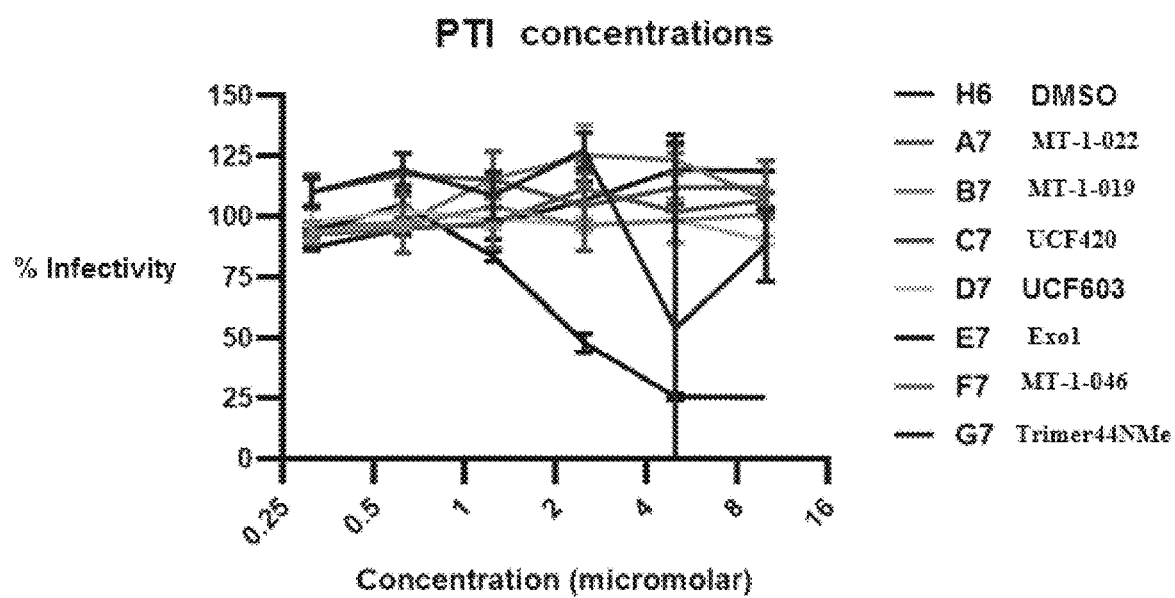
FIG. 4. Antiviral activity of trimer44NMe PTI compound 14 blocking infectivity of Ebola virus (G7 entry)

It is disclosed herein that this approach is applicable to viruses. While there have been some papers describing modulation of polyamine metabolism as a potential antiviral approach,[5, 14] there have been no papers describing the use of polyamine transport inhibitors (PTIs) as antivirals. Since the native polyamine spermidine (see FIG. 1, compound 2) is required to form the eukaryotic initiation factor 5A (eIF-5A) which is necessary for protein translation,[15] then strategies which deplete polyamine or spermidine pools or limit polyamine access in the host should stress and likely inhibit the ability of the virus to replicate and survive. The data provided herein demonstrates this to be true and it is now shown that the use of the PTI agent alone is sufficient to inhibit viral infection by Ebola virus (FIG. 4) or by the SARS-Cov2 virus (FIG. 5).

Figure 7:
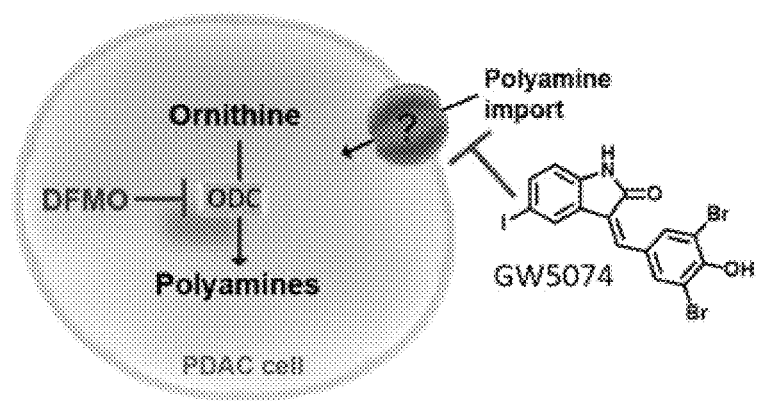
FIG. 7. Structure and mechanism of GW5074

In an alternative embodiment, non-polyamine based polyamine transport inhibitors may be used in accordance with the methods described herein. FIG. 7 shows an example of a non-polyamine PTI, GW5074[18].

Definitions

The term "co-administration" or "co-administering" as used herein refers to the administration of an active agent before, concurrently, or after the administration of another active agent such that the biological effects of either agent overlaps. The combination of agents as taught herein can act synergistically to treat or prevent the various diseases, disorders or conditions described herein. Using this approach, one may be able to achieve therapeutic efficacy with lower dosages of each agent, thus reducing the potential for adverse side effects.

The term "infection" as used herein refers to the presence of a virus in or on a subject, which if replication of the virus was retarded or the activity of the virus was reduced, would result in a benefit to the subject. Accordingly, the term "infection" refers to the presence of pathogens at any anatomical site of a human or animal.

As used herein, the term "pharmaceutically acceptable salt" refers to those salts which retain the biological effectiveness and properties of the active ingredient of the biochemical composition, which are not otherwise undesirable. Amines can be protonated by various acids to form protonated amine salts (e.g., $R_1R_2R_3NH^+/X^-$) which are often used to improve shelf-life and impart stability to the composition of matter. Pharmaceutically acceptable salts include, but are not limited to, salts formed after combination of the amine compound with inorganic acids like hydrochloric acid, or organic carboxylic acids such as oxalic acid or acetic acid to form oxalate or acetate salts, respectively. The pharmaceutically acceptable carrier may include pharmaceutically-acceptable material, composition or vehicle, such as a liquid or solid filler, diluent, excipient, solvent or encapsulating material, involved in carrying or transporting the compositions of the invention from one organ, or portion of the body, to another organ, or portion of the body without affecting its biological effect. Each carrier should be "acceptable" in the sense of being compatible with the other ingredients of the composition and not injurious to the subject.

As used herein, the term "therapeutically effective amount" refers to an amount of a composition of the disclosure that when administered to a human subject in need thereof, is sufficient to effect treatment or prophylaxis for virus infection. The amount that is therapeutically effective will depend upon the patient's size and gender, the stage and severity of the infection and the result sought. The full therapeutic effect does not necessarily occur by administration of one dose and may occur only after administration of a series of doses. Thus, a therapeutically effective amount may be administered in one or more administrations per day for successive days. For a given patient and condition, a therapeutically effective amount can be determined by methods known to those of skill in the art. For example, in reference to the treatment of a Sars-CoV2 virus infection using the compositions of the present invention, a therapeutically effective amount refers to that amount of the composition which has the effect of (1) reducing the shedding of the virus, (2) reducing the duration of the infection, (3) reducing infectivity and/or, (4) reducing the severity (or, preferably, eliminating) one or more other symptoms associated with the infection such as, for example, fever, headache, fatigue, dry cough, sore throat, respiratory distress, muscle aches, conjunctivitis, runny and/or stuffy nose. Such an effective dose will generally depend on the factors described above. A prophylactically effective dose is one that reduces the likelihood of contracting a virus infection.

The term, "pharmaceutically acceptable carrier" as used herein means a pharmaceutically-acceptable material, composition or vehicle, such as a liquid or solid filler, diluent, excipient, solvent or encapsulating material, involved in carrying or transporting the compositions of the invention from one organ, or portion of the body, to another organ, or portion of the body without affecting its biological effect. Each carrier should be "acceptable" in the sense of being compatible with the other ingredients of the composition and not injurious to the subject.

The term "treating" or "treatment of" as used herein refers to providing any type of medical management to a subject. Treating includes, but is not limited to, administering a composition comprising one or more active agents to a subject using any known method. for purposes such as curing, reversing, alleviating, reducing the severity of, inhibiting the progression of, or reducing the likelihood of a disease, disorder, or condition or one or more symptoms or manifestations of a disease, disorder or condition. The administration of the drug can be oral, nasal, parental, topical, ophthalmic, or transdermal administration or delivery in the form of solid, semi-solid, lyophilized powder, or liquid dosage forms. The dosage forms include tablets, capsules, troches, powders, solutions, suspensions, suppositories, or the like, preferably in unit dosage forms suitable for simple administration of precise dosages.

Pharmaceutical Formulations and Administration

The present invention also includes pharmaceutical compositions and formulations of polyamine transport inhibitors. In typical embodiments, pharmaceutical compositions comprise therapeutically effective amounts of at least one PTI, which amounts treat or prevent viral infection in a subject. Pharmaceutical compositions for use in the present methods include therapeutically effective amounts of one or more PTIs, i.e., an amount sufficient to prevent or treat the diseases described herein in a subject, formulated for local or systemic administration. There may be instances where two PTIs of different structure (e.g., one hydrophilic like compound $14^{13}$ and one lipophilic like AMXT1501$^{16}$) are combined as one therapy in order to reach specific compartments within the subject for better therapeutic outcomes. The subject is preferably a human but can be non-human as well. A suitable subject can be an individual who is suspected of having, has been diagnosed as having, or is at risk of developing a viral infection.

The duration of treatment can extend over several days or longer, depending on the condition, with the treatment continuing until the viral infection is sufficiently reduced or eliminated. PT's for therapeutic administration are preferably low in toxicity. The progress of this therapy is easily monitored by conventional techniques and assays that may be used to adjust dosage to achieve a desired therapeutic effect.

A composition of the PTI(s) can also include a pharmaceutically acceptable carrier. PTI containing compositions may contain, for example, such normally employed additives as binders, fillers, carriers, preservatives, stabilizing agents, emulsifiers, buffers and excipients as, for example, pharmaceutical grades of mannitol, lactose, starch, magnesium stearate, sodium saccharin, cellulose, magnesium carbonate, and the like. These compositions typically contain 1%-95% of active ingredient, preferably 2%-70% active ingredient.

The PTI(s) can also be mixed with diluents or excipients which are compatible and physiologically tolerable as selected in accordance with the route of administration and standard pharmaceutical practice. Suitable diluents and excipients are, for example, water, saline, dextrose, glycerol, or the like, and combinations thereof. In addition, if desired, the compositions may contain minor amounts of auxiliary substances such as wetting or emulsifying agents, stabilizing or pH buffering agents.

The formulations may also contain more than one active compound as necessary for the particular indication being treated, preferably those with complementary activities that do not adversely affect each other. Such molecules are suitably present in combination in amounts that are effective for the purpose intended.

Suitable examples of sustained release preparations include semipermeable matrices of solid hydrophobic polymers containing the therapeutic agents, which matrices are in the form of shaped articles, e.g., films, or microcapsule. Examples of sustained release matrices include, but are not limited to, polyesters, hydro gels (for example, poly (2-hydroxyethyl-methacrylate), or poly (vinylalcohol)), polylactides, copolymers of L-glutamic acid and ethyl-L-glutamate, non-degradable ethylene-vinyl acetate, degradable lactic acid-glycolic acid copolymers such as the LUPRON DEPOT (injectable micro spheres composed of lactic acid-glycolic acid copolymer and leuprolide acetate), and poly-D-(–)-3-hydroxybutyric acid. While polymers such as ethylene-vinyl acetate and lactic acid-glycolic acid enable release of molecules for over 100 days, certain hydrogels release proteins for shorter time periods.

The PTI agent may be formulated for administration by any suitable means. For in vivo administration, the pharmaceutical compositions are preferably administered orally or parenterally, i.e., intraarticularly, intravenously, intraperitoneally, subcutaneously, or intramuscularly. In particular embodiments, the pharmaceutical compositions are administered intravenously or intraperitoneally by a bolus injection. Stadler, et al., U.S. Pat. No. 5,286,634. For the prevention or treatment of disease, the appropriate dosage will depend on the severity of the disease, whether the drug is administered for protective or therapeutic purposes, previous therapy, the patient's clinical history and response to the drugs and the discretion of the attending physician.

The resulting pharmaceutical preparations may be sterilized by conventional, well known sterilization techniques. The aqueous solutions can then be packaged for use or filtered under aseptic conditions and lyophilized, the lyophilized preparation being combined with a sterile aqueous solution prior to administration. The compositions may contain pharmaceutically acceptable auxiliary substances as required to approximate physiological conditions, such as pH adjusting and buffering agents, tonicity adjusting agents and the like, for example, sodium acetate, sodium lactate, sodium chloride, potassium chloride, calcium chloride, etc. Additionally, the lipidic suspension may include lipid-protective agents which protect lipids against free-radical and lipid-peroxidative damages on storage. Lipophilic free-radical quenchers, such as α-tocopherol and water-soluble iron-specific chelators, such as ferrioxamine, are suitable.

The pharmaceutical compositions of this invention may be in a variety of forms, which may be selected according to the preferred modes of administration. These include, for example, solid, semi-solid and liquid dosage forms such as tablets, lozenge, pills, powders, liquid solutions or suspensions, suppositories, and injectable and infusible solutions. The preferred form depends on the intended mode of administration and therapeutic application. For oral administration, the PTI may be formulated as dispersible tablet, orally disintegrating tablet, effervescent tablet, chewable tablet, sprinkle granules, dry suspension or dry syrup for reconstitution, quick melt wafers, lozenge, or chewing gum.

The pharmaceutical compositions of this invention may, for example, be placed into sterile, isotonic formulations with or without cofactors which stimulate uptake or stability. The formulation is preferably liquid, or may be lyophilized powder. For example, the compositions of the invention may be diluted with a formulation buffer comprising 5.0 mg/ml citric acid monohydrate, 2.7 mg/ml trisodium citrate, 41 mg/ml mannitol, 1 mg/ml glycine and 1 mg/ml polysorbate 20. This solution can be lyophilized, stored under refrigeration and reconstituted prior to administration with sterile Water-For-Injection (USP).

Any of the compositions described herein may be comprised in a kit. In a non-limiting example, a PTI is included in a kit. The kit may further include water and buffer. The components of the kits may be packaged either in aqueous media or in lyophilized form. The container means of the kits will generally include at least one vial, test tube, flask, bottle, syringe or other container means, into which a component may be placed, and preferably, suitably aliquoted. Where there is more than one component in the kit (labeling reagent and label may be packaged together), the kit also will generally contain a second, third or other additional container into which the additional components may be separately placed. However, various combinations of components may be comprised in a vial. The kits of the present invention also will typically include a means for containing the agents, and any other reagent containers in close confinement for commercial sale. Such containers may include injection or blow-molded plastic containers into which the desired vials are retained.

When the components of the kit are provided in one and/or more liquid solutions, the liquid solution is an aqueous solution, with a sterile aqueous solution being particularly preferred. However, the components of the kit may be provided as dried powder(s). When reagents and/or components are provided as a dry powder, the powder can be reconstituted by the addition of a suitable solvent. It is envisioned that the solvent may also be provided in another container means.

The container will generally include at least one vial, test tube, flask, bottle, syringe and/or other container means, into which the nucleic acid formulations are placed, preferably, suitably allocated. The kits may also comprise a second container for containing a sterile, pharmaceutically acceptable buffer and/or other diluent.

Such kits may also include components that preserve or maintain the antagonists or that protect against their degradation. Such kits generally will comprise, in suitable means, distinct containers for each individual reagent or solution. A kit will also include instructions for employing the kit components as well the use of any other reagent not included in the kit. Instructions may include variations that can be implemented. A kit may also include utensils or devices for administering the antagonist by various administration routes, such as parenteral or catheter administration or coated stent.

Suitable Solvates Include Hydrates. Suitable salts include those formed with both organic and inorganic acids or bases. Pharmaceutically acceptable base salts include ammonium salts, alkali metal salts such as those of sodium and potassium, alkaline earth metal salts such as those of calcium and magnesium and salts with organic bases such as dicyclohexylamine and N-methyl-D-glucamine.

Formulations for parenteral administration include aqueous and non-aqueous sterile injection solutions, which may contain anti-oxidants, buffers, bacteriostats and solutes which render the formulation isotonic with the blood of the intended recipient; and aqueous and non-aqueous sterile suspensions which may include suspending agents and thickening agents. The formulations may be presented in unit-dose or multi-dose containers, for example sealed ampoules and vials, and may be stored in a freeze-dried (lyophilized) condition requiring only the addition of the sterile liquid carrier, for example saline or water-for-injection, immediately prior to use. Extemporaneous injection solutions and suspensions may be prepared from sterile powders, granules and tablets of the kind previously described.

Spray compositions for delivery to the lung by inhalation may for example be formulated as aqueous solutions or suspensions or as aerosols delivered from pressurized packs, such as a metered dose inhaler, with the use of a suitable liquefied propellant. Aerosol compositions suitable for inhalation can be either a suspension or a solution of the therapeutic and a suitable.

Medicaments for administration by inhalation desirably have a controlled particle size. The optimum particle size for inhalation into the bronchial system is usually 1-10 μm, preferably 2-5 μm. Particles having a size above 20 μm are generally too large when inhaled to reach the small airways.

It will be understood that the methods and uses of the invention may be employed prophylaxis as well as (more suitably) in the treatment of subjects suffering from viral infection.

PTIs may be co-administered with another PTI or with an active agent (e.g., PTI in combination with another active agent such as DFMO and/or another antiviral agent) and may be administered simultaneously meaning the administration of agents such that the agents are present within a subject such that biological effects overlap. Co-administration of the agents may be occur via the same or alternative routes at the same time or via the same or an alternative route at different times.

The invention has been described with reference to specific embodiments. It will, however, be evident that various modifications and changes may be made thereto without departing from the broader spirit and scope of the invention. The specification and drawings are, accordingly, to be regarded in an illustrative rather than a restrictive sense. The invention is illustrated herein by the experiments described above and by the following examples, which should not be construed as limiting. The contents of all references, pending patent applications and published patents, cited throughout this application are hereby expressly incorporated by reference. Although specific terms are employed, they are used as in the art unless otherwise indicated.

EXAMPLES

Example 1: Chemistry

The synthesis of the lead PTI (trimer44NMe) is shown in Scheme 1 and has already been patented in prior disclosures.

Scheme 1[a]

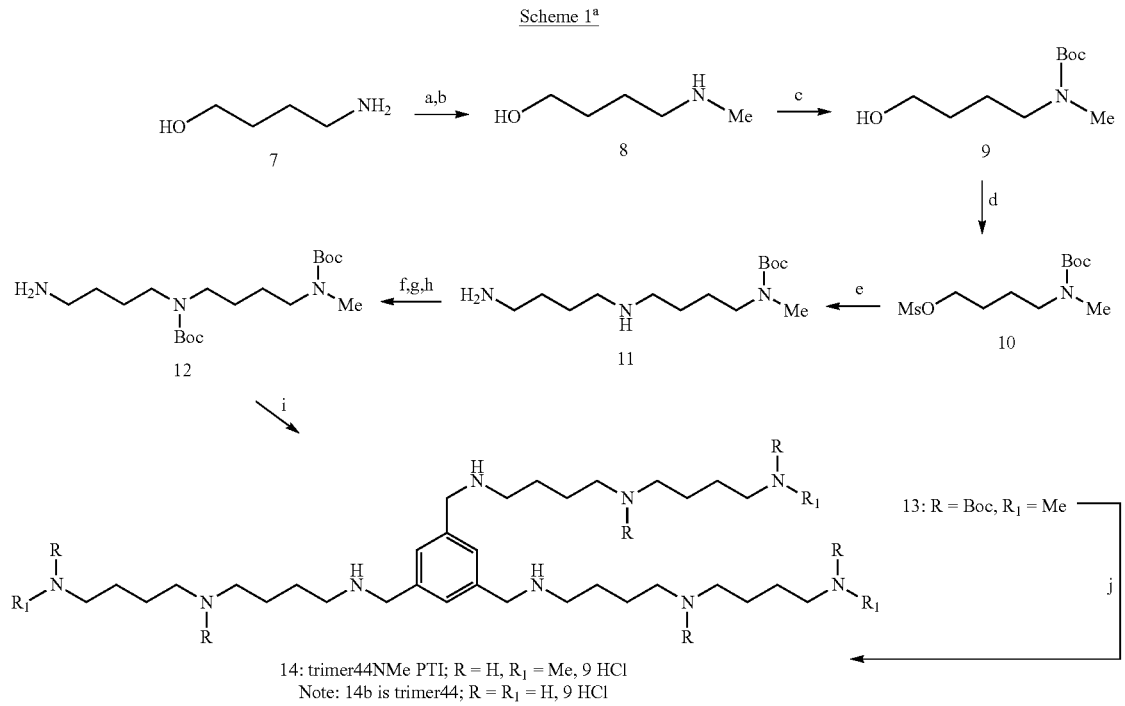

14: trimer44NMe PTI; R = H, R₁ = Me, 9 HCl
Note: 14b is trimer44; R = R₁ = H, 9 HCl

[a]Reagents: (a) Ethyl formate, EtOH; (b) LiAlH$_4$, THF; (c) di-tert-butyl dicarbonate, 10% TEA/MeOH; (d) MsCl, TEA, CH$_2$Cl$_2$; (e) putrescine (5 equiv), K$_2$CO$_3$, CH$_3$CN; (f) salicylaldehyde, Na$_2$SO$_4$, 25% MeOH/CH$_2$Cl$_2$; (g) di-tert-butyl dicarbonate, MeOH; (h) CH$_3$ONH$_2$; i) benzene-1,3,5-tricarboxaldehyde, NaBH$_4$; j) 4M HCl, EtOH Other derivatives of the lead PTI compound (trimer44NMe) have also been made which are believed to be active (like 14b in Scheme 1) and 15-17 in FIG. 2. Their syntheses and bioevaluation as PTIs have been published.[13] It was also shown that 14 is a competitive inhibitor of polyamine uptake using radiolabeled spermidine ($K_i$=55 nM).[13, 17]

These PTI designs provide a comprehensive collection of multivalent polyamine architectures for inhibition of polyamine transport and are predicted to have antiviral activity like 14. While 3-armed designs like 14 work, it is expected that other systems with 2, 4, or five polyamine "arms" may also function as PTIs as they have multiple arms to compete with the native polyamines for cell entry.

Example 2: Biology

The following Figures show the PTI trimer44NMe exhibiting antiviral properties against Ebola virus (FIG. 4) and the SARS-CoV2 virus (FIG. 5).

REFERENCES

1. Pegg, A. E., Functions of Polyamines in Mammals. *J Biol Chem* 2016, 291 (29), 14904-14912.
2. Alexander, E. T.; Minton, A.; Peters, M. C.; Phanstiel, O. t.; Gilmour, S. K., A novel polyamine blockade therapy activates an anti-tumor immune response. *Oncotarget* 2017, 8 (48), 84140-84152.
3. Raina, A.; Tuomi, K.; Mantyjarvi, R., Roles of polyamines in the replication of animal viruses. *Med Biol* 1981, 59 (5-6), 428-432.
4. Tyms, A. S.; Williamson, J. D., Inhibitors of polyamine biosynthesis block human cytomegalovirus replication. *Nature* 1982, 297 (5868), 690-691.
5. Mounce, B. C.; Poirier, E. Z.; Passoni, G.; Simon-Loriere, E.; Cesaro, T.; Prot, M.; Stapleford, K. A.; Moratorio, G.; Sakuntabhai, A.; Levraud, J. P.; Vignuzzi, M., Interferon-Induced Spermidine-Spermine Acetyltransferase and Polyamine Depletion Restrict Zika and Chikungunya Viruses. *Cell Host Microbe* 2016, 20 (2), 167-177.
6. Mounce, B. C.; Olsen, M. E.; Vignuzzi, M.; Connor, J. H., Polyamines and Their Role in Virus Infection. *Microbiol Mol Biol Rev* 2017, 81 (4).
7. Sutherland, C. S.; Yukich, J.; Goeree, R.; Tediosi, F., A literature review of economic evaluations for a neglected tropical disease: human African trypanosomiasis ("sleeping sickness"). *PLoS Negl Trop Dis* 2015, 9 (2), e0003397.
8. Mounce, B. C.; Cesaro, T.; Moratorio, G.; Hooikaas, P. J.; Yakovleva, A.; Werneke, S. W.; Smith, E. C.; Poirier, E. Z.; Simon-Loriere, E.; Prot, M.; Tamietti, C.; Vitry, S.; Voile, R.; Khou, C.; Frenkiel, M. P.; Sakuntabhai, A.; Delpeyroux, F.; Pardigon, N.; Flamand, M.; Barba-Spaeth, G.; Lafon, M.; Denison, M. R.; Albert, M. L.;

Vignuzzi, M., Inhibition of Polyamine Biosynthesis Is a Broad-Spectrum Strategy against RNA Viruses. *J Virol* 2016, 90 (21), 9683-9692.
9. Olsen, M. E.; Cressey, T. N.; Muhlberger, E.; Connor, J. H., Differential Mechanisms for the Involvement of Polyamines and Hypusinated eIF5A in Ebola Virus Gene Expression. *J Virol* 2018, 92 (20).
10. Alexander, E. T.; Minton, A.; Peters, M. C.; Phanstiel, O.; Gilmour, S. K., A novel polyamine blockade therapy activates an anti-tumor immune response. *Oncotarget* 2017, 8 (48), 84140-84152.
11. Hayes, C. S.; Burns, M. R.; Gilmour, S. K., Polyamine blockade promotes antitumor immunity. *Oncoimmunology* 2014, 3 (1), e27360.
12. Hayes, C. S.; Shicora, A. C.; Keough, M. P.; Snook, A. E.; Burns, M. R.; Gilmour, S. K., Polyamine-blocking therapy reverses immunosuppression in the tumor microenvironment. *Cancer immunology research* 2014, 2 (3), 274-285.
13. Muth, A.; Madan, M.; Archer, J. J.; Ocampo, N.; Rodriguez, L.; Phanstiel, O., Polyamine transport inhibitors: design, synthesis, and combination therapies with difluoromethylornithine. *J Med Chem* 2014, 57 (2), 348-363.
14. Tate, P. M.; Mastrodomenico, V.; Mounce, B. C., Ribavirin Induces Polyamine Depletion via Nucleotide Depletion to Limit Virus Replication. *Cell Rep* 2019, 28 (10), 2620-2633 e4.
15. Park, M. H.; Wolff, E. C., Hypusine, a polyamine-derived amino acid critical for eukaryotic translation. *The Journal of biological chemistry* 2018, 293 (48), 18710-18718.
16. Samal, K.; Zhao, P.; Kendzicky, A.; Yco, L. P.; McClung, H.; Gerner, E.; Burns, M.; Bachmann, A. S.; Sholler, G., AMXT-1501, a novel polyamine transport inhibitor, synergizes with DFMO in inhibiting neuroblastoma cell proliferation by targeting both ornithine decarboxylase and polyamine transport. *Int J Cancer* 2013, 133 (6), 1323-1333.
17. Madan, M.; Patel, A.; Skruber, K.; Geerts, D.; Altomare, D. A.; Phanstiel, O., ATP13A3 and caveolin-1 as potential biomarkers for difluoromethylornithine-based therapies in pancreatic cancers. *Am J Cancer Res* 2016, 6 (6), 1231-1252.
18. Dobrovolskaite A, Madan M, Pandey V, Altomare D A, Phanstiel O 4th. The discovery of indolone GW5074 during a comprehensive search for non-polyamine-based polyamine transport inhibitors. Int J Biochem Cell Biol. 2021 September; 138:106038. doi: 10.1016/j.biocel.2021.106038. Epub 2021 Jul. 9. PMID: 34252566.

What is claimed is:

1. A method of treating an infection by a Ebola virus, SARS-CoV1 or Sars-CoV-2 virus in a subject in need comprising administering a composition comprising at least at least one of compounds (i)-(xix):

(i)

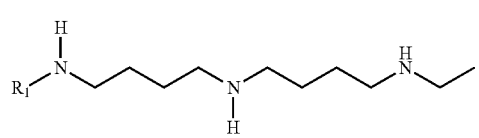

(ii)

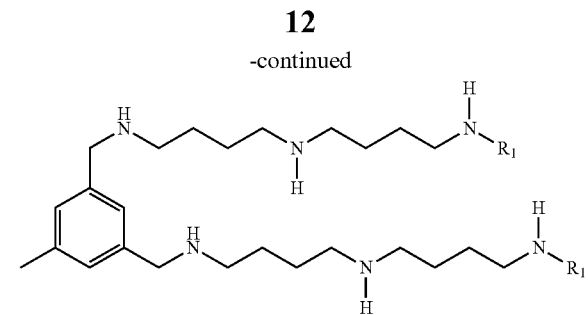

wherein R1 is Me or H;

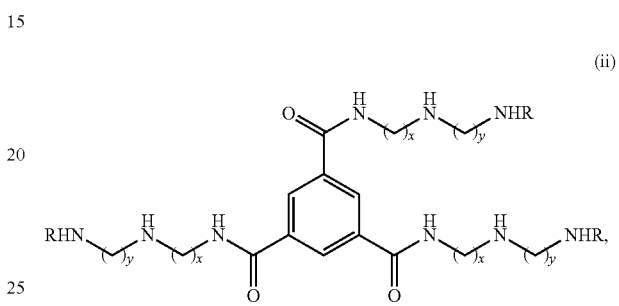

wherein R is H and x and y are both 4, or R is $(CH_2)_4NH_2$ and x and y are both 4, or R is $(CH_2)_3NH_2$, x is 3, and y is 4;

(iii)

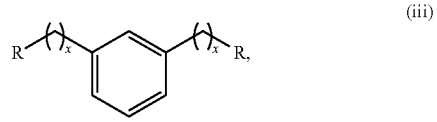

wherein x is 1 or 2;

(iv)

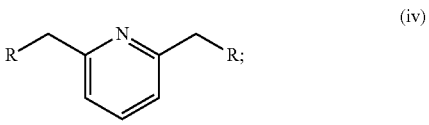

(v)

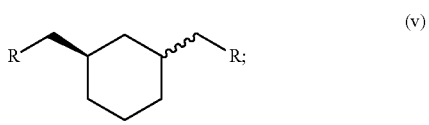

(vi)

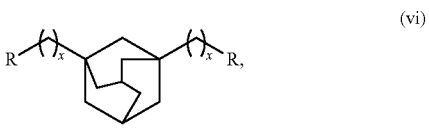

wherein x is 1 or 2;

(vii)

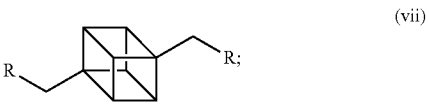

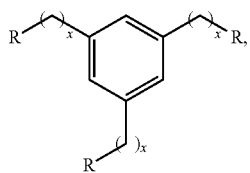

wherein x is 2;

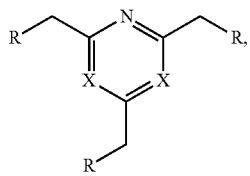

wherein X is CH or N;

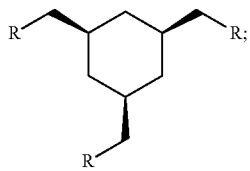

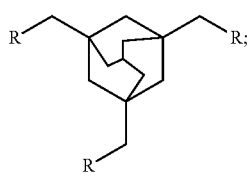

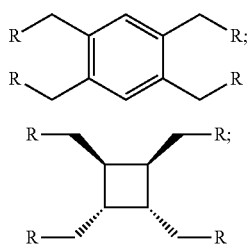

wherein X is OH or H;

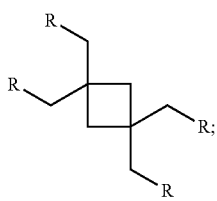

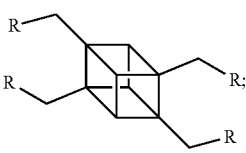

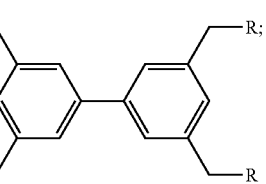

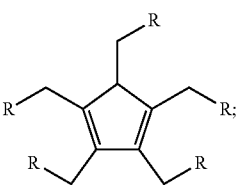

wherein R in compounds iii-xix is $NH(CH_2)_4NH(CH_2)_4NHMe$; or a pharmaceutically acceptable salt of any of compounds i-xix, and, optionally

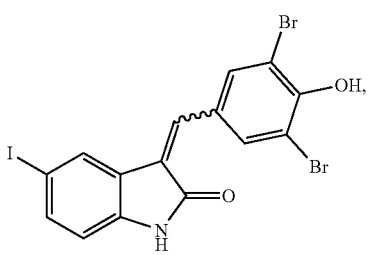 [SMILES: O=C1Nc2ccc(I)cc2C1=Cc1cc(Br)c(O)c(Br)c1]

or a pharmaceutically acceptable salt thereof, and optionally a pharmaceutically acceptable carrier.

2. The method of claim 1, further comprising co-administering at least one other active agent, wherein the at least one other active agent is AMXT1501, GW5074, DFMO, methylcyclohexylamine and $N^1$ Cyclohexyl-1,3-diaminopropane or CGP-48664 or a combination thereof.

3. The method of claim 1, further comprising co-administering at least one agent comprising remdesivir, chloroquine, hydroxychloroquine, entecavir, cabotegravir, rilpivirine, stavudine, valganciclovir, or cidofovir.

4. The method of claim 1, wherein the composition is formulated for oral administration.

5. The method of claim 4, wherein the composition is in the form of a dispersible tablet, orally disintegrating tablet, effervescent tablet, chewable tablet, sprinkle granules, dry suspension or dry syrup for reconstitution, quick melt wafers, lozenge, or chewing gum.

6. The method of claim 1, wherein the composition is formulated for parenteral administration.

7. The method of claim 6, wherein the composition is in the form of a liquid suspension or solution.

8. A composition comprising at least one of compounds (i)-(xix):

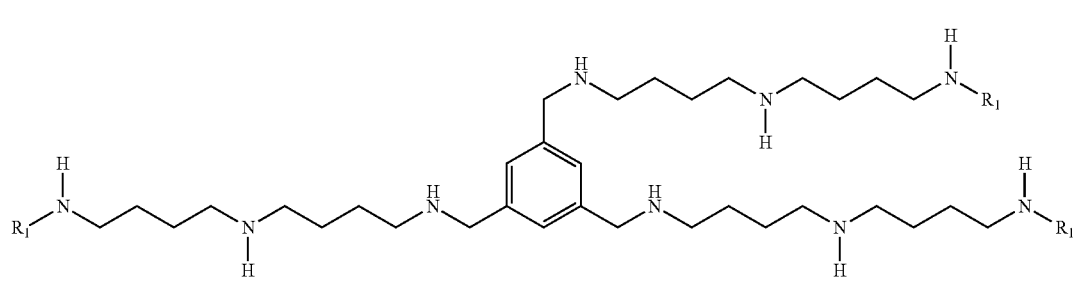

wherein R1 is Me or H;

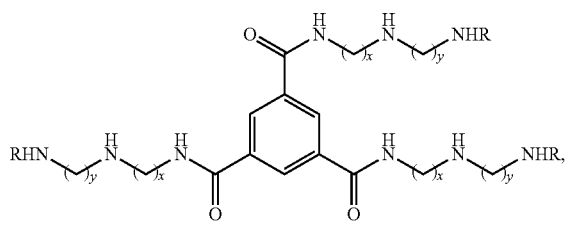

wherein R is H and x and y are both 4, or R is $(CH_2)_4NH_2$ and x and y are both 4, or R is $(CH_2)_3NH_2$, x is 3, and y is 4;

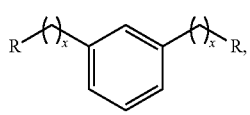

wherein x is 1 or 2;

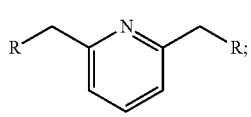

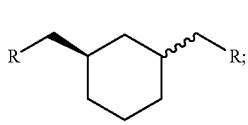

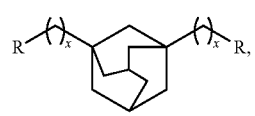

wherein x is 1 or 2;

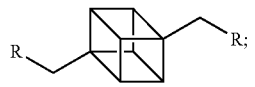

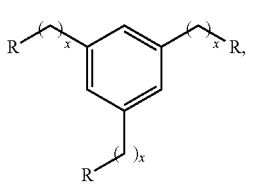

wherein x is 2;

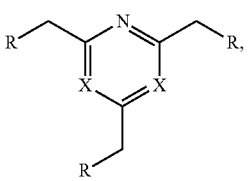

wherein X is CH or N;

(x)
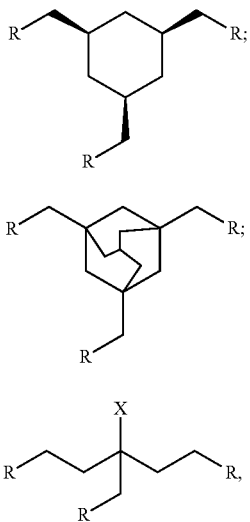

(xi)

(xii)

wherein X is OH or H;

(xiii)

(xiv)

(xv)

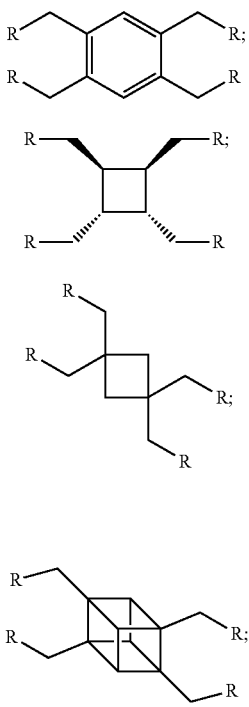

(xvi)

(xvii)

(xviii)

(xix)

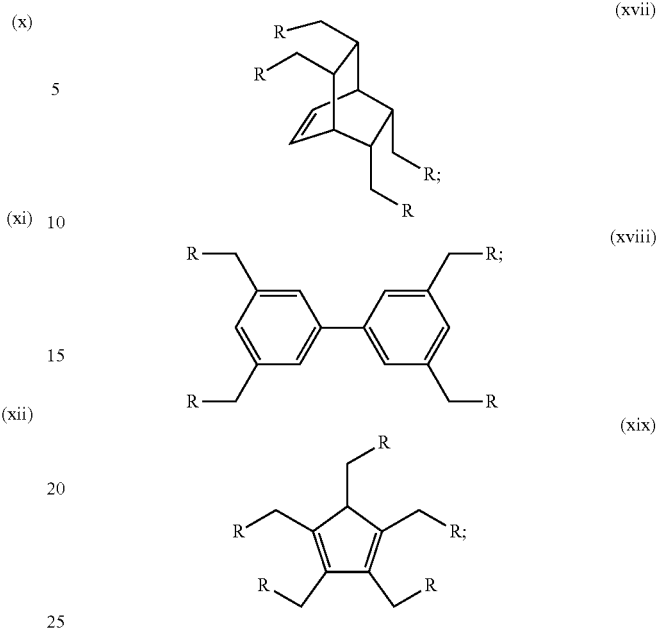

wherein R in compounds iii-xix is $NH(CH_2)_4NH(CH_2)_4NHMe$; or a pharmaceutically acceptable salt of any of compounds i-xix, and further comprising

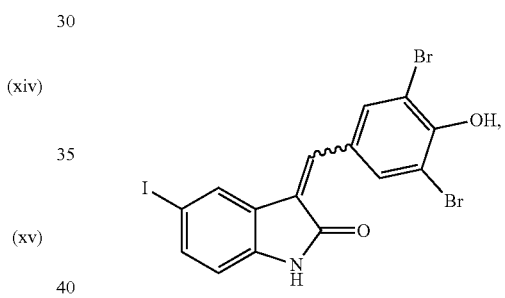

or a pharmaceutically acceptable salt thereof.

9. The composition of claim 8 further comprising at least one of remdesivir, chloroquine, hydroxychloroquine, entecavir, cabotegravir, rilpivirine, stavudine, valganciclovir, or cidofovir.

10. The composition of claim 8, formulated for oral administration.

11. The composition of claim 10, wherein the composition is in the form of a dispersible tablet, orally disintegrating tablet, effervescent tablet, chewable tablet, sprinkle granules, dry suspension or dry syrup for reconstitution, quick melt wafers, lozenge, or chewing gum.

12. The composition of claim 8, formulated for parenteral administration.

* * * * *